United States Patent
Salamone et al.

(10) Patent No.: US 7,459,281 B2
(45) Date of Patent: *Dec. 2, 2008

(54) DOCETAXEL IMMUNOASSAY

(75) Inventors: Salvatore J. Salamone, Stockton, NJ (US); Jodi Blake Courtney, Doylestown, PA (US); Gregory Drake Lundell, Easton, PA (US); Mahmoud Ahmed ElSohly, Oxford, MS (US); Waseem Gul, Oxford, MS (US)

(73) Assignee: Saladax Biomedical Inc., Bethlehem, PA (US)

( * ) Notice: Subject to any disclaimer, the term of this patent is extended or adjusted under 35 U.S.C. 154(b) by 22 days.

This patent is subject to a terminal disclaimer.

(21) Appl. No.: 11/384,848

(22) Filed: Mar. 20, 2006

(65) Prior Publication Data

US 2006/0216769 A1 Sep. 28, 2006

Related U.S. Application Data

(63) Continuation-in-part of application No. 11/087,008, filed on Mar. 22, 2005, now abandoned.

(51) Int. Cl.
| G01N 33/53 | (2006.01) |
| G01N 33/532 | (2006.01) |
| G01N 33/551 | (2006.01) |
| C07K 16/00 | (2006.01) |
| C07K 1/13 | (2006.01) |
| C07K 1/04 | (2006.01) |
| C07D 305/14 | (2006.01) |

(52) U.S. Cl. .......... 435/7.93; 435/7.1; 436/523; 436/524; 436/544; 436/548; 436/815; 530/388.9; 530/389.8; 530/402; 530/403; 549/510

(58) Field of Classification Search .......... 435/7.1, 435/7.93; 530/388.9, 389.8, 402, 403; 436/544, 436/548, 523, 524, 815; 549/510
See application file for complete search history.

(56) References Cited

U.S. PATENT DOCUMENTS

| 5,981,777 A | 11/1999 | Durzan et al. |
| 6,080,877 A | 6/2000 | Swindell et al. |
| 7,175,993 B2 | 2/2007 | Salamone et al. |
| 2006/0216767 A1* | 9/2006 | Salamone et al. .......... 435/7.92 |

FOREIGN PATENT DOCUMENTS

EP 696596 A1 2/1996

OTHER PUBLICATIONS

The International Search Report and Written Opinion of the Internatioanl Searching Authority, issued on Mar. 14, 2007, in the PCT application No. PCT/US06/09957.
Office Action dated Jul. 2, 2007 for parent U.S. Appl. No. 11/087,008.

* cited by examiner

Primary Examiner—Long V. Le
Assistant Examiner—Shafiqul Haq

(57) ABSTRACT

Novel conjugates of docetaxel and novel docetaxel immunogens derived from the 7 and 10 positions of docetaxel and monoclonal antibodies generated by these docetaxel linked immunogens are useful in immunoassays for the quantification and monitoring of docetaxel in biological fluids.

18 Claims, No Drawings

DOCETAXEL IMMUNOASSAY

CROSS-REFERENCE TO RELATED APPLICATIONS

This application is a Continuation-In-Part of Ser. No. 11/087,008, filed Mar. 22, 2005 now abandoned.

FIELD OF THE INVENTION

This invention relates to the field of immunological assays for determining the presence and/or quantifying the amount of docetaxel in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Taxotere, whose chemical name is docetaxel, is a common cytotoxic agents used for the treatment of breast, androgen independent prostate and non-small cell lung cancer. Docetaxel, which is also known as Taxotere, has the formula:

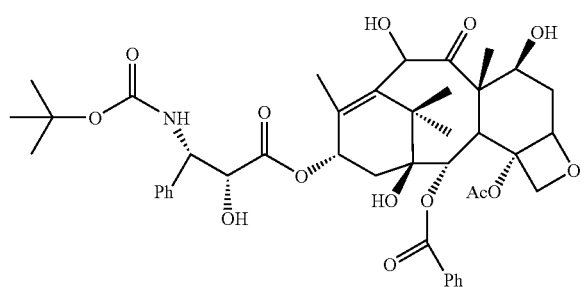

I

This compound has been associated with debilitating side effects such as bone marrow density loss, allergic reaction, neutropenia, nausea and vomiting. By monitoring the levels of docetaxel in the body and adjusting the dose these side effects can be better controlled and limited in patients.

At the same time, there is often highly variable relationship between the dose of docetaxel and the resulting serum drug concentration that affects therapeutic effect. The degree of intra- and inter-individual pharmacokinetic variability of docetaxel can be as high as 4-fold and is impacted by many factors, including:
  Organ function
  Genetic regulation
  Disease state
  Age
  Drug-drug interaction
  Time of drug ingestion,
  Mode of drug administration
  Technique-related administration As a result of this variability, equal doses of the same drug in different individuals can result in dramatically different clinical outcomes (Hon et. al. *Clinical Chemistry* 44, pp 388-400, 1998). The effectiveness of the same docetaxel dosage varies significantly based upon individual drug clearance and the ultimate serum drug concentration in the patient. Therapeutic drug management would provide the clinician with insight on patient variation in intravenous drug administration. With therapeutic drug management, drug dosages could be individualized to the patient, and the chances of effectively treating the cancer, without the unwanted side effects, would be much higher.

In addition, therapeutic drug management of docetaxel would serve as an excellent tool to ensure compliance in administering chemotherapy with the actual prescribed dosage and achievement of the effective serum concentration levels. It has been found that variability in serum concentration is not only due to physiological factors, but can also result from variation in administration technique.

Routine therapeutic drug management of docetaxel would require the availability of simple automated tests adaptable to general laboratory equipment. Tests that best fit these criteria are immunoassays. In order to be an effective immunoassay antibodies will have to be developed which are reactive with the active form of the drug. Currently there are no immunoassays available for determining levels of docetaxel in plasma or blood.

SUMMARY OF INVENTION

In accordance with this invention, a new class of antibodies have been produced which are substantially reactive with docetaxel so as to bind to docetaxel.

It has been found that by using immunogens which are conjugates of an immunogenic carrier with a ligand selected from the group consisting of a 10-hydroxydocetaxel derivatives of the formula:

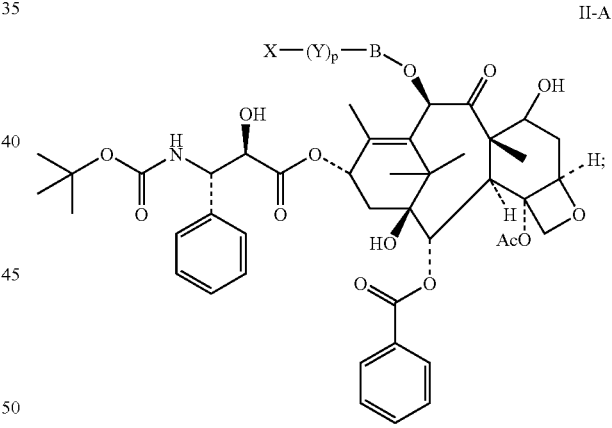

7-hydroxydocetaxel derivatives of the formula:

7,10-dihydroxy docetaxel derivatives of the formula:

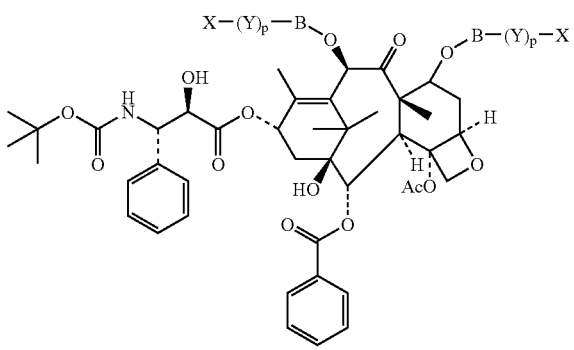

II-C wherein B is —CH$_2$—; or

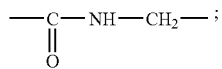

Y is an organic spacing group;
X is a functional group capable of binding to a cater; and
p is an integer from 0 to 1;

or mixtures thereof, produce antibodies which are reactive with docetaxel. The provision of these antibodies which react with docetaxel, allows one to produce an immunoassay which can specifically detect and monitor docetaxel in the fluid samples of patients being treated with docetaxel. Also included within this invention are reagents and kits for said immunoassay.

DETAILED DESCRIPTION

In accordance with this invention, a new class of antibodies is provided which reacts with docetaxel. It has been discovered that through the use of these docetaxel derivatives of formula II-A, II-B or II-C or mixtures thereof; as immunogens, this new class of antibodies of this invention are provided. It is through the use of these antibodies that an immunoassay, including reagents and kits for such immunoassay for detecting and/or quantifying docetaxel in blood, plasma or other body fluid samples has been developed. By use of this immunoassay, the presence and amount of docetaxel in body fluid samples, preferably a blood or plasma sample, can be detected and/or quantified. In this manner, a patient being treated with docetaxel, can be monitored during therapy and treatment adjusted in accordance with said monitoring. By means of this invention one achieves the therapeutic drug management of docetaxel in cancer patients being treated with docetaxel as a chemotherapeutic agent. The preferred antibodies are those which are reactive with docetaxel and not substantially cross-reactive with taxol and pharmaceutically inactive docataxel related compounds sent us 10-O-deacetyl-baccatin III.

The reagents utilized in the assay of this invention are conjugates of a carrier, preferably containing polyamine functional groups, with the compounds of formula II-A, II-B and II-C or mixtures thereof. These conjugates are competitive binding partners with the docetaxel present in the sample for the binding with the antibodies of this invention. Therefore, the amount of conjugate reagent which binds to the antibody will be inversely proportional to the amount of docetaxel in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of docetaxel in a sample is determined by correlating the measured amount of the bound or unbound conjugate produced by the docetaxel in the sample with values of the bound or unbound conjugate determined from standard or calibration curve samples containing known amounts of docetaxel, which known amounts are in the range expected for the sample to be tested. These studies for producing calibration curves are determined using the same immunoassay procedure as used for the sample.

The conjugates, as well as the immunogens, are prepared from compounds of the formula II-A, II-B and II-C or mixtures thereof. In the conjugates or immunogens, the carrier and the polyamine polymer are linked to ligand portions of the compounds of formula II-A, II-B and II-C. The ligand portions have the formula:

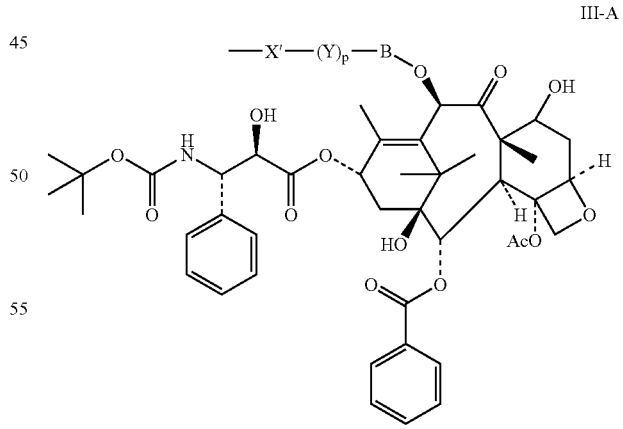

III-A wherein Y, B and p are as above; and
x' is —CH$_2$— or a functional linking group;

compounds of the formula:

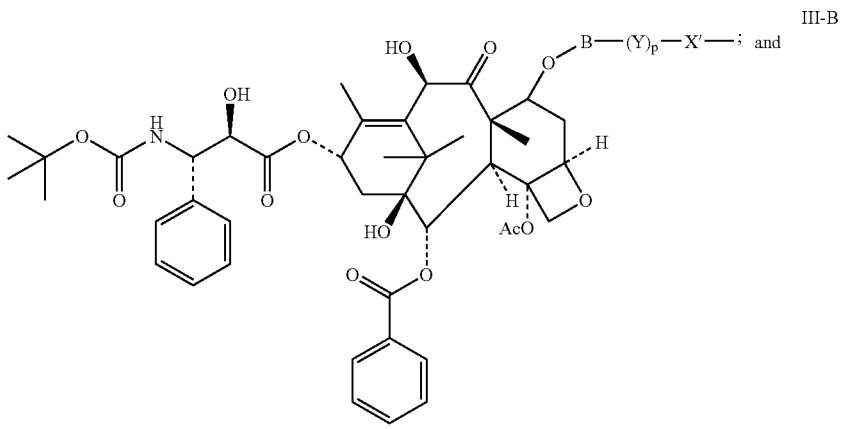

compounds of the formula:

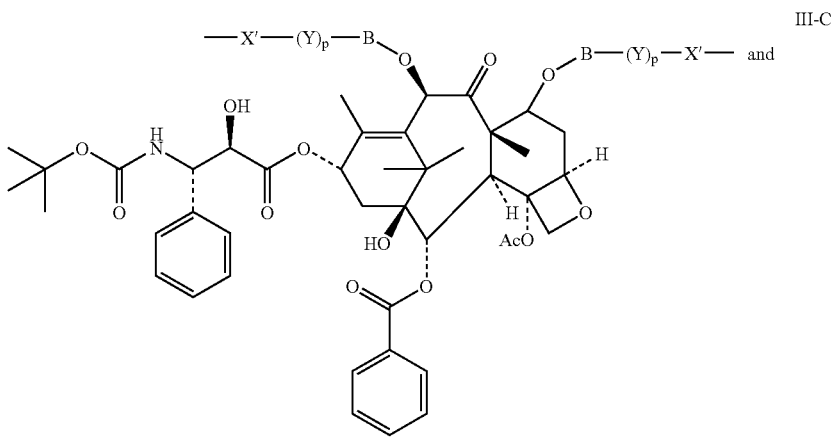

These ligand portions may be linked to one or more active sites on the carrier of the conjugate or the immunogen. Generally these carriers contain polymers, most preferably polyamine polymers having a reactive amino group. In forming the conjugates, X is preferably a functional group which can react with an amino group. When the compounds of formula II-A, II-B or II-C are used to make immunogens, X in the compound of formula II-A, II-B and II-C is preferably any functional group capable of binding or linking to a polyamine polymer.

Definitions

Throughout this description the following definitions are to be understood:

The term "alkylene" designates a divalent saturated straight or branch chain hydrocarbon substituent containing from one to ten carbon atoms The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II-A, II-B and II-C and a large molecule, such as a carrier, preferably carriers which comprise a polyamine polymer, particularly a protein. In the conjugate the small molecule maybe joined or linked at one or more active sites on the large molecule. The term conjugate includes the term immunogen. In the conjugates used as reagents the carrier can be any carrier and X can be any functional group which can be linked to a carrier. In the immunogen the carrier is a polyamine polymer and X is any functional group capable of linling to a polyamine polymer.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is docetaxel.

As used herein, a "spacing group" or "spacer" refers to a portion of a chemical structure which connects two or more substructures such as haptens, carriers, immunogens, labels, or tracer through a CH2 or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case docetaxel or the docetaxel derivatives hereinbefore described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are high molecular weight polymers built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli,* and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of a-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to the polymeric material which preferably is a polyamine polymer to provide one or more reactive sites for bonding to the terminal functional group X in the compounds of the formula II-A, II-B and II-C.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for docetaxel. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate of docetaxel is constructed to compete with the docetaxel in the sample for binding sites on the antibodies. In the immunoassay of this invention, the reagents are conjugates of a carrier with a) the 10-substituted docetaxel derivatives of the compounds of formula II-A; b) the 7-docetaxel derivatives of formula II-B and c) the 7,10-disubstituted derivatives of docetaxel of formula II-C or mixtures thereof. In the compounds of formula III-A, III-B and III-C, the linker spacer constitutes the "—B—$(Y)_p$—X'—" portion of this molecule. The linker X' and the spacer "—B—$(Y)_p$—" are conventional in preparing conjugates and immunogens. Any of the conventional spacer-linking groups utilized to prepare conjugates and immunogens for immunoassays can be utilized in the compounds of formula III-A, III-B and III-C. Such conventional linkers and spacers are disclosed in U.S. Pat. Nos. 5,501,987 and 5,101,015.

Among the preferred spacer groups are included the spacer groups hereinbefore mentioned. Particularly preferred spacing groups are groups such as alkylene containing from 1 to 10 carbon atoms,

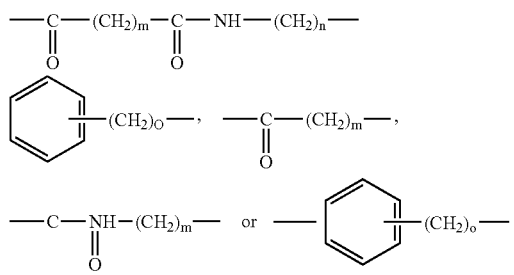

wherein n and o are integers from 0 to 6, and m is an integer from 1 to 6 with alkylene being the especially preferred spacing group.

In the compounds of formula III-A, III-B and III-C, X' is —$CH_2$— or a functional group linking the spacer to the carrier, preferably to an amine group on the polymeric carrier. The group X' is the result of the terminal functional group X in the compounds of Formula II-A, II-B and II-C which is capable of binding to a carrier, preferably to an amino group in the polyamine polymer present in the carrier or used as the immunogen. Any terminal functional group capable of binding to a carrier, preferably capable of reacting with an amine can be utilized as the functional group X in the compounds of formula II-A, II-B, and II-C. These terminal functional groups preferably included within X are:

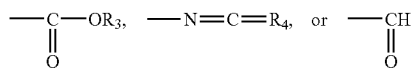

wherein $R_3$ is hydrogen or taken together with its attached oxygen atom forms a reactive ester and $R_4$ is oxygen or sulfur. The radical —N=C=$R_4$, can be an isocyanate or an isothiocyanate. The active esters formed by $OR_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention. On the other hand, carriers can be coated with a polyamine polymer to supply the amino group for linking to the ligand portion.

In the immunogens and conjugates of the present invention, the chemical bonds between the carboxyl group-containing docetaxel haptens and the amino groups on the polyamine polymer on the carrier or immunogen can be established using a variety of methods known to one skilled in the art. It is frequently preferable to form amide bonds. Amide bonds are formed by first activating the carboxylic acid moiety of the docetaxel hapten in the compounds of formula II-A, II-B and II-C by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the docetaxel hapten of formula II-A, II-B and II-C is then reacted with a buffered solution containing the protein carrier.

In cases where the docetaxel derivative of formula II-A, II-B and II-C contains a primary or secondary amino group as well as the carboxyl group, it is necessary to use an amine protecting group during the activation and coupling reactions to prevent the conjugates from reacting with themselves. Typically, the amines on the conjugate are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. Nos. 3,996,344 and 4,016,146, which are herein incorporated by reference.

On the other hand where X is a terminal isocyanate or isothiocyanate radical in the compound of formula II-A, II-B and II-C, these radicals when reacted with the free amine of a polyamine polymer produce the conjugate or the immunogen where X' is,

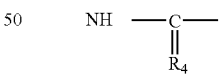

in the ligand portions of formula III-A, III-B and III-C, functionally connects with the amino group on the polyamine containing carrier or the immunogenic polypeptide.

Where X, in the compounds of formula II-A, II-B and II-C, is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula III-A, III-B and III-C is —$CH_2$—.

In preparing the 7- and -10-monoderivatives of formula II-A and II-B and the 7,10-di substituted derivatives of docetaxel, the 2'-hydroxy group of docetaxel is first protected. This 2'-hydroxy group is on the side chain extending from the 13-position on the docetaxel ring structure. This is the most reactive of the hydroxy groups in docetaxel. Any conventional method of protecting a hydroxy group such as by an esterification can be utilized to protect this hydroxy group at the 2' position, while leaving the hydroxy groups at the 7 and 10 positions free for reaction. Any of the conventional hydroxy protecting groups can be utilized to accomplish this purpose. A preferred hydroxy protecting group is the allylorthoformate ester group which is formed by reacting the compound of formula I with allylchloroformate by conventional means well known in the art. This is an easily produced protecting group which can be easily removed at a later stage in the process.

After protecting the 2' hydroxy group, this protected docetaxel of formula I can be converted into the 10-docetaxel derivative of formula II-A, the 7-docetaxel derivative of formula II-B or the 7,10-docetaxel derivative of formula II-C depending upon the molar quantity of reagents utilized to react with the 2' protected docetaxel of formula I. In general, where a molar excess of the reagent is reacted with the 2' protected docetaxel of formula I, the resulting final product will be a mixture of the 7-O and 10-O substituted derivatives, as well as the 7,10-O disubstituted derivatives. These derivatives can be separated using a silica gel column and a gradient comprising dichloromethane and ethyl acetate, generally 100% dichloromethane at the start while gradually adding ethyl acetate to the column. The individual ingredients can be collected and their structure confirmed by NMR.

In carrying out this reaction the 7 hydroxy group in the 2' hydroxy protected docetaxel will react first with the reagent such as the compound of formula V-A. Therefore, by limiting the ratio of the reagent such as the compound of formula V-A or VI which is reacted with the compound of formula I to about 0.9 to 1.5 moles per mole, the final product will substantially consist of the compounds of formula II-B. Increasing the mole ratio of the reagents reacted with the 2' protected hydroxy docetaxel of formula I will produce more of the compounds of formula II-A and II-C in the product. These derivatives can be separated from the product as described above.

The 10 and 7-substituted derivatives of formula II-A and II-B where B is —CH$_2$—, as well as the 7,10-disubstituted derivatives of formula II-C are formed by reacting the 7 and 10-hydroxy group of docetaxel with a halide of the formula:

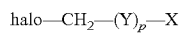  V-A wherein p, Y and X are as above.

In forming these derivatives, any conventional means of reacting an alcohol to form an ether can be utilized in condensing the compound of formula V-A with the 7-hydroxy position on the docetaxel. The use of a halide in the compound of formula V-A provides an efficient means for forming an ether by condensing with the alcohol. On the other hand, where the compound of formula V-A contains functional groups, which may interfere with this reaction to form these derivatives, these functional groups can be protected by means of suitable protecting groups which can be removed after this reaction as described hereinabove.

The above derivatives of formula II-A, II-B or II-C where B is

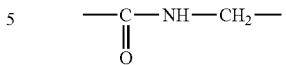

are produced by reacting one or more of the free hydroxy groups on the 2' protected docetaxel with an amino compound of the formula:

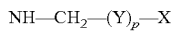  VI wherein X, Y and p are as above, after first converting the one or more hydroxy groups on the 2' protected docetaxel to the chloroformate group

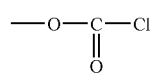

Any conventional means of converting a hydroxy group to a chloroformate group can be used. After the formulation of a chloroformate, the halo group of the chloroformate is condensed with the amine group in the compound of formula VI. Prior to this reaction, the reactive group on docetaxel and/or on the compound of formula VI are protected as described hereinabove with a conventional protecting group. These protecting groups can be removed after this halide condensation by conventional means such as described hereinbefore.

The compounds of formula II-A, II-B and II-C can be converted into the immunogens and/or the conjugate reagents of this invention by reacting these compounds with a carrier, preferably a polyamine polypeptide or a carrier coated with a polyamine polypeptide. The same polypeptide can be utilized as the carrier and as the immunogenic polymer in the immunogen of this invention provided that polyamines or polypeptides are immunologically active. However, to form the conjugates used as reagents in the immunoassay, these polymers need not produce an immunological response as needed for the immunogens. In accordance with this invention, the various functional group represented by X in the compounds of formula II-A, II-B and II-C can be conjugated to the carrier by conventional means of attaching a functional group to a carrier. In accordance with a preferred embodiment, in the compounds of formula II-A, II-B and II-C, X is a carboxylic acid group.

Antibodies

The present invention also relates to novel antibodies including monoclonal antibodies to docetaxel produced by utilizing the aforementioned immunogens. In accordance with this invention it has been found that these antibodies produced in accordance with this invention are reactive with docetaxel and do not substantially react with metabolites of docetaxel derivatives which would interfere with immunoassays for docetaxel. In addition the antibodies of this invention do not substantially react with taxol, whose chemical name is paclitaxel and docetaxel like compounds such as 10-O-Deacetylbaccatin III which contain the docetaxel or taxol ring structure. The compound 10-O-Deacetylbaccatin III has the formula:

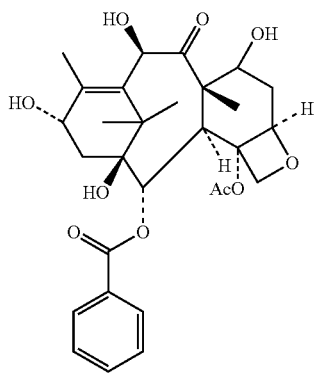

The present invention relates to novel antibodies and monoclonal antibodies to docetaxel. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals. Through periodic bleeding, the blood samples of the immunized mice were observed to develop an immune response against docetaxel binding utilizing conventional immunoassays. These methods provide a convenient way to screen for hosts and antibodies which are producing antisera having the desired activity. The antibodies were also screened against taxol and antibodies were produced which showed no substantial binding to taxol.

Monoclonal antibodies are produced conveniently by immunizing Balb/c mice according to the schedule followed by injecting the mice with additional immunogen i.p. or i.v. on three successive days starting three days prior to the cell fusion. Other protocols well known in the antibody art may of course be utilized as well. The complete immunization protocol detailed herein provided an optimum protocol for serum antibody response for the antibody to docetaxel.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell. Murine hybridomas which produce docetaxel monoclonal antibodies are formed by the fusion of mouse myeloma cells and spleen cells from mice immunized with the aforementioned immunogenic conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutageneses to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are reactive with docetaxel. In addition, the preferred antibodies do not have any substantial cross-reactivity with taxol or 10-O-deacetylbaccatin III. By substantial cross-reactivity it is meant that the antibodies of this invention have a cross reactivity relative to docetaxel with taxol or 10-O-deacetylbaccatin III of 20% or less.

Immunoassays

In accordance with this invention, the conjugates and the antibodies generated from the immunogens of the compounds of formula II-A, II-B and II-C or mixtures thereof can be utilized as reagents for the determination of docetaxel in patient samples. This determination is performed by means of an immunoassay. Any immunoassay in which the reagent conjugates formed from the compounds of formula II-A, II-B and II-C compete with the docetaxel in the sample for binding sites on the antibodies generated in accordance with this invention can be utilized to determine the presence of docetaxel in a patient sample. The manner for conducting such an assay for docetaxel in a sample suspected of containing docetaxel, comprises combining an (a) aqueous medium sample, (b) an antibody to docetaxel generated in accordance with this invention and (c) the conjugates formed from the compounds of formula II-A, II-B and II-C or mixtures thereof. The amount of docetaxel in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of docetaxel. In determining the amount of docetaxel in an unknown sample, the sample, the conjugates formed from the compounds of formula II-A, II-B and II-C and the antibody may be added in any order.

Various means can be utilized to measure the amount of conjugate formed from the compounds of formula II-A, II-B and II-C bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. Nos. 4,269, 511 and 4,420,568.

On the other hand, the antibody can be coated or absorbed on nanoparticles so that when these particles react with the docetaxel conjugates formed from the compounds of formula II-A, II-B and II-C, these nanoparticles form an aggregate. However, when the antibody coated or absorbed nanoparticles react with the docetaxel in the sample, the docetaxel from the sample bound to these nanoparticles does not cause aggregation of the antibody nanoparticles. The amount of aggregation or agglutination can be measured in the assay mixture by absorbance.

On the other hand, these assays can be carried out by having either the antibody or the docetaxel conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula II-A, II-B and II-C which is bound or unbound with the antibody. Other suitable labels include chromophores, fluorophores, etc.

As a matter of convenience, assay components of the present invention can be provided in a kit, a packaged combination with predetermined amounts of new reagents employed in assaying for docetaxel. These reagents include the antibody of this invention, as well as, the conjugates formed from the compounds of formula II-A, II-B and II-C or mixtures thereof. It is generally preferred that in a given immunoassay, if a conjugate formed from a compound of formula II-B is utilized, that the antibody be generated by an immunogen formed from a compound of formula II-B. In a like manner, if a conjugate formed from a compound of formula II-B or II-C is utilized, the antibody be generated by the immunogen formed from the same compound is used for the conjugate. However, this need not be the case and antibodies and conjugates in a given assay can be derived from any one or of these conjugates and immunogens. In carrying out an immunoassay in accordance with this invention the radicals p, X, Y and B in the reagent and the immunogen which forms the antibody used in a given immunoassay can be the same or be a different substituent within the groups defined for each of theses radicals. Therefore while the definitions of the radicals p, X, Y, and B are the same for the conjugate reagent and the immunogen, the particular substituent which these radicals represent for the immunogen and the conjugate reagent in a given assay may be different.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the Examples, the following abbreviations are used for designating the following:

| | |
|---|---|
| EA | Ethyl alcohol |
| MeOH | Methanol |
| EtOAc | Ethyl acetate |
| DCM | Dichloromethane |
| DMAP | Dimethylaminopyridine |
| Et$_3$N | Triethyl amine |
| NHS | N-hydroxy-succinimide |
| EDC | 1-(3-dimethylaminopropyl)-3-ethylcarbodiimide hydrochloride |
| TLC | Thin Layer Chromatography |
| KLH | Keyhole Limpet Hemocyanin |
| ANS | 8-Anilino-1-naphthalenesulfonic acid |
| i.p. | Intraperitoneal |
| HRP | Horse radish-peroxidase |
| TMB | 3,3',5,5'-Tetramethylbenzidine |
| TRIS | Tris(hydroxymethyl)aminomethane hydrochloride |
| BSA | Bovine serum albumin |
| BTG | Bovine thyroglobulin |
| PBS | Phosphate buffered saline |
| HEPES | 4-(2-Hydroxyethyl)piperazine-1-ethanesulfonic acid |
| di | deionized water |

In the Examples, Scheme 1 and Scheme 2 below set forth the specific compounds prepared and referred to by numbers in the Examples. The schemes are as follows:

Scheme 1

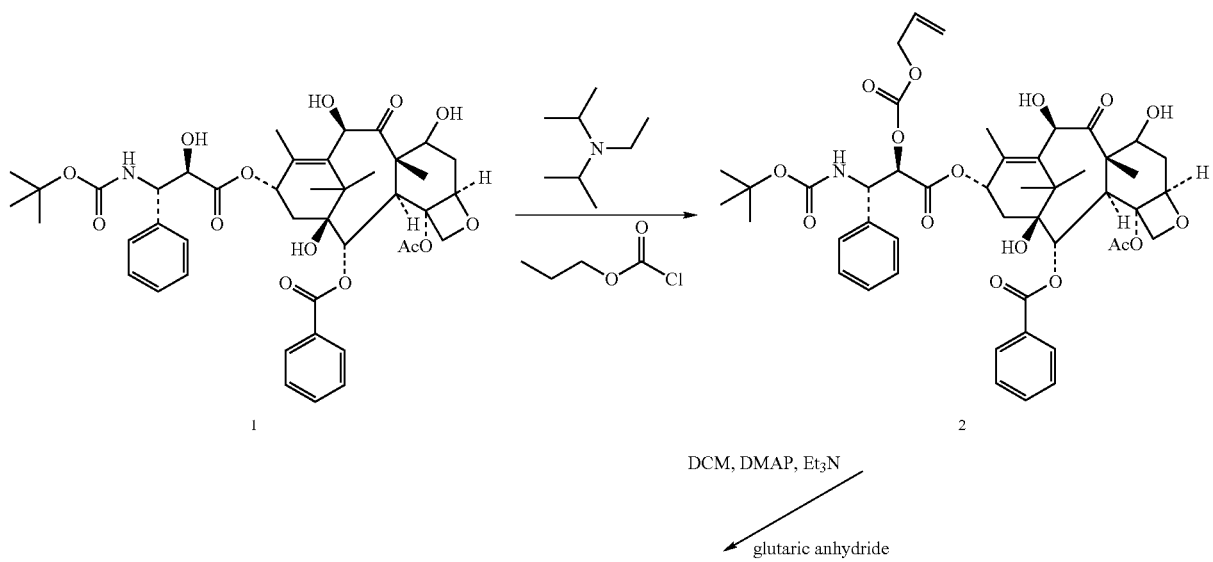

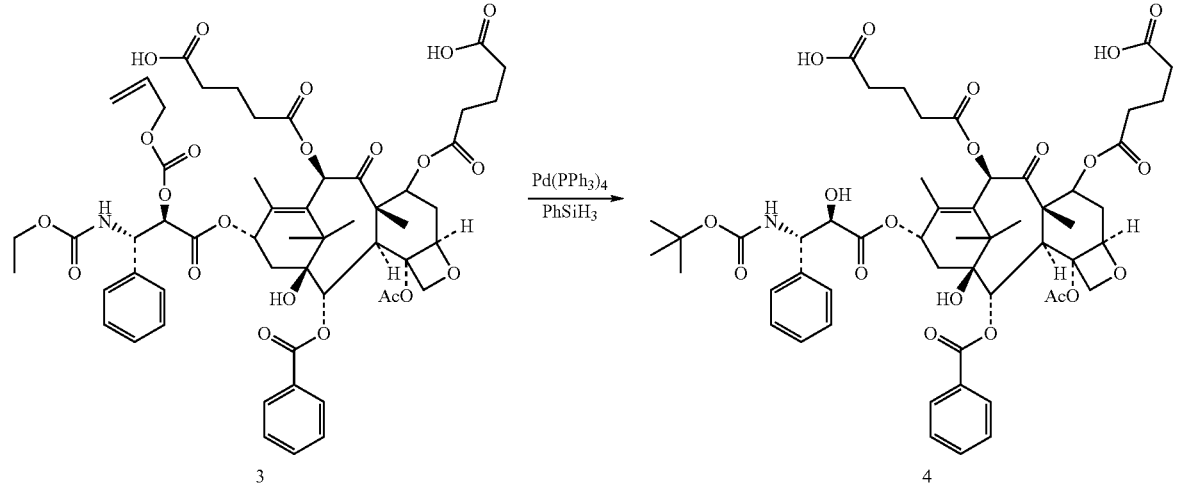
Scheme 2
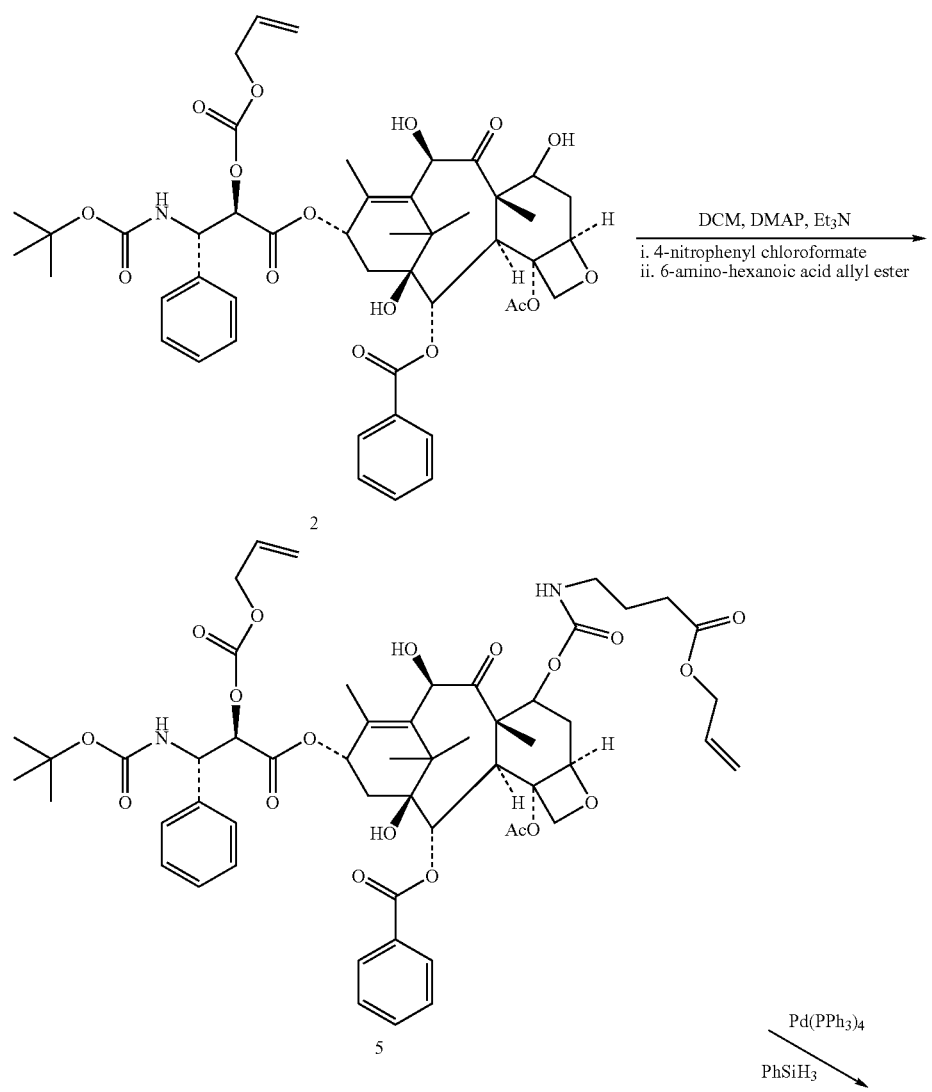

-continued

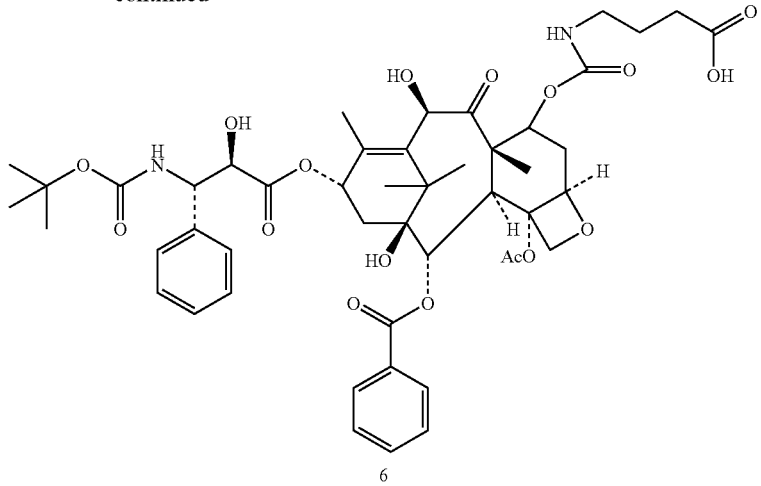

6

EXAMPLES

Example 1

Preparation of C7, C10 Docetaxel Di-acid Derivative [4] Scheme I

Docetaxel [I] (500 mg) was added to a three-neck flask in 20 mL of freshly distilled dichloromethane, under a continuous flow of argon. The temperature was maintained at −15° C., at which time diisopropylethylamine (2 eq.) and allyl chloroformate (1.1 eq.) were added. The reaction mixture temperature was brought to room temperature and allowed to stir for 5 hours. 20 mL of dichloromethane was added and the mixture was washed with 0.1N HCl (60 mL), dried on $Na_2SO_4$, and concentrated on a rotary evaporator. Crude material was purified on a silica gel column with EtOAc/DCM as the gradient (30% EtOAc:71% DCM) to yield [2] (468 mg, 84.78%) as an off-white solid. To a solution of the alloc-protected docetaxel, [2], (511 mg, 0.57 mmol) and DMAP (0.22 mmol) in DCM (50 mL) under nitrogen, $Et_3N$ (0.22 mmol) was added followed by addition of glutaric anhydride (2 eq). The resulting mixture was allowed to stir overnight at room temperature. DCM was removed under vacuum and the crude material was purified on a silica gel column with EtOAc/DCM gradient (40% EtOAc:60% DCM) to yield [3] (194 mg, 30.23%) as an off-white solid. Derivative [3] (0.173 mmol) was dissolved in 6 mL of dichloromethane under argon and then $PhSiH_3$ (1.04 mmol) was added along with Pd $(PPh_3)_4$ (0.008 mmol). After 4 hours, 1.5 mL of MeOH was added and the mixture was stirred for an additional 10 minutes. The reaction mixture was evaporated to dryness to yield the deprotected docetaxel derivative [4].

Derivative [4] was purified on a silica gel column (60% EtOAc:40% DCM as solvent system) to separate this derivative from the presence of the other derivatives such as the 7-mono docetaxel derivate and the 10-mono docetaxel derivative. The derivative [4] was isolated as an off white gum (145.1 mg, 80.86%), 24.25% calculated from starting material and its structure was confirmed by NMR.

Example 2

Preparation of Activated C7, C10 Docetaxel Di-acid Derivative from Compound [4]

The diglutaric acid derivative [4] (125.1 mg, 0.121 mmol) was dissolved in 10 mL of dry DMSO. With stirring under nitrogen N-hydroxysulfosuccinimide sodium salt (114.7 g, 0.528 mmol, 4.4 eq) was added followed by EDC (102.4 mg, 0.534 mmol, 4.4 eq). The reaction was stirred overnight at room temperature when additional EDC was added (96 mg, 0.501 mmol, 4.15 eq). After 7 hours of continued stirring at room temperature the reaction was complete by TLC. The TLC condition was ethyl acetate : dichloromethane (3:2) with 2 drops of acetic acid.

Example 3

Preparation of Docetaxel-BSA Conjugate with Activated C7, C10 Docetaxel Di-acid Derivative (1:1 Ratio)

To a 20 mL solution of BSA (50 mg/mL) in 50 mM phosphate buffer (50 mM, pH 7.5) with stirring on ice, was added drop wise 1.34 mL (0.016 mmol) of the activated N-hydroxysulfosuccinimide ester docetaxel derivative prepared in Example 2. The reaction mixture was allowed to stir overnight at room temperature to produce the di-acid conjugate to BSA. This conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 4

Preparation of C7, C10 Docetaxel Di-acid Derivative Immunogen with BTG

To a 6.1 mL solution of BTG (32.9 mg/mL) in phosphate buffer (50 mM, pH 7.5) with stirring on ice, was added drop wise 5.1 mL (0.0617 mmol) of the of the activated N-hydroxysulfosuccinimide ester docetaxel derivative prepared in Example 2. The reaction mixture was allowed to stir overnight at room temperature to produce the di-acid conjugate to BTG. The immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 5

Preparation of C7, C10 Docetaxel Di-acid Derivative Immunogen with KLH

To a 5.4 mL solution of KLH (8.9 mg/mL) in phosphate buffer (50 mM, pH 7.5) with stirring on ice, was added drop wise 5.1 mL (0.0145 mmol) of the activated N-hydroxysulfosuccinimide ester docetaxel derivative prepared in Example 2. The reaction mixture was allowed to stir overnight at room temperature to produce the di-acid conjugate to KLH. The immunogenic conjugate was then purified by dialysis and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 6

Preparation of C7 Substituted Docetaxel Acid Derivative [6] Scheme II

To a solution of alloc-protected docetaxel, [2], (201 mg, 0.23 mmol) and DMAP (110 mg, 0.9 mmol) in DCM (6 mL) under nitrogen, $Et_3N$ (0.9 mmol, 0.13 mL) was added followed by p-nitrophenyl chloroformate (54.6 mg, 0.27 mmol). The reaction mixture was stirred at room temperature for 3.5 hours and then a solution of 6-amino-hexanoic acid allyl ester (52.6 mg, 0.29 mmol) in DCM (2 mL) was added. The resulting mixture was stirred overnight at room temperature. DCM was removed in vacuo and the crude material was purified on silica gel column with EtOAc/hexanes as the gradient (Rf=0.39, 50% EtOAc/hexanes) to yield [5] (81.4 mg, 35%) as an off-white gum.

To a solution of [5] (100 mg, 0.094 mmol) and $Pd(PPh_3)_4$ (15.3 mg, 0.013 mmol) in DCM (6 mL) under nitrogen was added a solution of $PhSiH_3$ (40.8 mg, 0.38 mmol) in DCM (1 mL). The resulting mixture was stirred overnight at room temperature. DCM was removed and the crude material was purified on a silica gel column with MeOH/DCM as the gradient (Rf=0.2, 10% MeOH/DCM) to give [6] (39.6 mg, 41%) as a tan gum and its structure was confirmed by NMR.

Example 7

Preparation of Activated C7 Substituted Docetaxel Acid Derivative from Compound [6]

Derivative [6] (39.6 mg, 0.042 mmol) was dissolved in 5 mL of dry DCM. With stirring under nitrogen NHS (14.5 mg, 0.126 mmol, 3.0 eq) was added followed by EDC (24.0 mg, 0.126 mmol, 3.0 eq). The reaction was stirred for 29 hours at room temperature and was then quenched by the addition of HCl (3 mL, 0.3 N) and 15 mL of DCM. The mixture was stirred for 10 minutes and the organic layer was separated, dried ($Na_2SO_4$), filtered and the DCM was removed in vacuo to yield an off white amorphous solid.

Example 8

Preparation of Docetaxel-BSA Conjugate with Activated C7 Substituted Docetaxel Acid Derivative (1:1 ratio)

The activated ester produced in Example 6 was dissolved in 700 µL of DMSO and 50 µL of this solution was added drop wise to 8 mL of a BSA solution (4 mL DMSO/4 mL 50 mM phosphate, pH 7.5). The solution was stirred for 24 hours at room temperature to produce the conjugate of BSA and the docetaxel derivative [6]. This conjugate was purified by dialysis according to procedures previously described (Wu et. al., Bioconj. Chem., 8: pp 385-390,1997, Li et.al., Bioconj. Chem., 8: pp 896-905, 1997, Salamone et.al., J. Forensic Sci. pp 821-826, 1998).

Example 9a

Preparation of C7 Substituted Docetaxel Acid Derivative Immunogen with BTG

To 6.3 mL of BTG (21.1 mg/mL) in 50 mM phosphate buffer (50 mM, pH 7.5) stirring on ice 12.6 mL DMSO was slowly added drop wise. To this solution, the activated NHS ester of the C7 substituted docetaxel (derivative [6]) prepared in Example 7 (650 µL, 62 mg/mL in DMSO) was added drop wise. The resulting mixture was allowed to stir overnight at room temperature to conjugate the BTG to the C7 docetaxel derivative. This immunogenic conjugate was then purified by dialysis and characterized according to procedures described previously (Wu et. al., Bioconj. Chem., 8: pp 385-390,1997, Li et.al., Bioconj. Chem., 8: pp 896-905, 1997, Salamone et.al., J. Forensic Sci. pp 821-826, 1998).

Example 9b

Preparation of C7 Substituted Docetaxel Acid Derivative Immunogen with KLH

To 27.02 mL of KLH (4.92 mg/mL) in 66.6% DMSO/43.4% 50 mM phosphate buffer (50 mM, pH 7.5) was added the activated NHS ester (of the C7 substituted docetaxel (derivative [6]) prepared in Example 7 (1,000 µL, 62 mg/mL in DMSO) was added drop wise. The resulting mixture was allowed to stir overnight at room temperature to conjugate the KLH to the C7 docetaxel derivative. This immunogenic conjugate was then purified by dialysis and characterized according to procedures described previously (Wu et. al., Bioconj. Chem., 8: pp 385-390, 1997, Li et.al., Bioconj. Chem., 8: pp 896-905, 1997, Salamone et.al., J. Forensic Sci. pp 821-826, 1998).

Example 10

Preparation of C7, C10 Docetaxel di-acid Derivative Antibodies

Ten Female BALB/c mice were immunized i.p. with 100 µg/mouse of docetaxel-immunogen: either docetaxel-BTG as prepared in Example 4 or docetaxel-KLH as prepared in Example 5, emulsified in Complete Freund's Adjuvant. After the initial injection mice were boosted four weeks after the preceding injection with 100 µg/mouse of the same immunogens emulsified in Incomplete Freund's Adjuvant. Six to ten days after the boosts test bleeds from each mouse were obtained by orbital bleed. The anti-serum from the last test bleeds containing docetaxel antibodies from each of the mice were evaluated by the procedures in Examples 14a and 15 to determine their reactivity to docetaxel and their cross reactivity to 10-O-Deacytlbaccatin III and, paclitaxel [Taxol]. Only the antiserum having antibodies which were selective for docetaxel and had a cross reactivity relative to docetaxel with 10-O-Deacytlbaccatin III and paclitaxel of 6% or less as determined by these screening procedures were selected.

Example 11

Preparation of C7 Substituted Docetaxel Acid Derivative Antibodies

Ten Female BALB/c mice were immunized i.p. with 100 µg/mouse of docetaxel-immunogen: either docetaxel-BTG as prepared in Example 9a or docetaxel-KLH immunogen as prepared in Example 9b emulsified in Complete Freund's Adjuvant. After the initial injection mice were boosted once after four weeks with 100 µg/mouse of the same immunogen emulsified in Incomplete Freund's Adjuvant. Ten days after the boosts test bleeds from each mouse were obtained by orbital bleed. The anti-serum from the last test bleeds containing docetaxel antibodies from each of the mice were evaluated by the procedures in Examples 14a and 16 to determine their reactivity to docetaxel and their cross reactivity to 10-O-Deacytlbaccatin III and, paclitaxel [Taxol]. Only the antiserum having antibodies which were selective for docetaxel and had a cross reactivity relative to docetaxel with 10-O-Deacytlbaccatin III and paclitaxel of 6% or less as determined by these screening procedures were selected.

For monoclonal antibodies starting four days before the fusion, the mice were injected i.p. with 400 µg (3 days before fusion), 200 µg (2 days before fusion), and 200 µg (1 day before fusion) on three successive days with either docetaxel-BTG or docetaxel-KLH (depending on the original immunogen) in PBS. According to the protocol of Coligan et al. spleen cells were isolated from the selected mice and fused with $2 \times 10^7$ cells of the myeloma fusion partner cell line ($SP_2$/o) using 50% polyethylene glycol 1500 [Coligan, J. E. et al., eds., Current Protocols in Immunology, 2.5.1-2.5.8, (1992), Wiley & Sons, N.Y.] To grow the fused cells into antibody producing colonies according to the method of Coligan et al. the fused cells were plated on 10 96-well plates in a conventional HAT (hypoxanthine, aminopterin and thymidine) selective growth medium such as DMEM/$F_{12}$ (Dulbecco's Modified Eagle's Medium 1:1 with L-glutamine and HEPES) supplemented with 20% fetal bovine serum alternative, and containing 2% L-glutamine (100 mM) and 2% 50×HAT. Two weeks later, the hybridoma supernatant was assayed for the presence of anti-docetaxel antibodies by ELISA as described in Example 14b. Positive wells were expanded and again screened by the same ELISA method. The positive clones were subcloned directly or confirmed for docetaxel binding by a competitive ELISA as described in Example 16. Clones positive by ELISA as described in Example 14b were subcloned once or twice by limiting dilution according to the method disclosed in Coligan, J. E. et al., eds., Current Protocols in Immunology, 2.5.8-2.5.17, (1992), Wiley & Sons, N.Y.

Only the monoclonal antibodies which were selective for docetaxel and had a cross reactivity relative to docetaxel with 10-O-Deacytlbaccatin III and paclitaxel of 15% or less as determined by these screening procedures were selected.

Example 12

Microtiter Plate Sensitization Procedure with C7, C10 Docetaxel Di-acid Derivative—BSA Conjugate For the purpose of screening antibodies and measuring docetaxel concentration by Enzyme-Linked Immunosorbent Assay (ELISA) method polystyrene microtiter plates optimized for protein binding and containing 96 wells per plate were used. Each well was coated with docetaxel-BSA conjugate (prepared as in Example 3) by adding 300 µL of docetaxel-BSA conjugate at 10 µg/mL in 0.05M sodium bicarbonate, pH=9.6, and incubating for three hours at room temperature. The wells were washed with 0.05M sodium bicarbonate, pH 9.6 and then were blocked with 400 µL of 5% sucrose, 0.2% sodium caseinate solution for 30 minutes at room temperature. After removal of the post-coat solution the plates were dried at 37° C. overnight.

Example 13

Microtiter Plate Sensitization Procedure with C7 Substituted Docetaxel Acid Derivative—BSA Conjugate For the purpose of screening antibodies and measuring docetaxel concentration by Enzyme-Linked Immunosorbent Assay (ELISA) method polystyrene microtiter plates optimized for protein binding and containing 96 wells per plate were used. Each well was coated with docetaxel-BSA conjugate (prepared as in Example 8) by adding 300 µL of docetaxel-BSA conjugate at 10 µg/mL in 0.05M sodium bicarbonate, pH=9.6, and incubating for three hours at room temperature. The wells were washed with 0.05M sodium bicarbonate, pH 9.6 and then were blocked with 400 µL of 5% sucrose, 0.2% sodium caseinate solution for 30 minutes at room temperature. After removal of the post-coat solution the plates were dried at 37° C. overnight.

Example 14a

Antibody Screening Procedure—Titer

Antibodies were screened by Enzyme-Linked Immunosorbent Assay (ELISA) method. This method for screening docetaxel antibodies (produced in Examples 10 and 11) was performed with the microtiter plates that were sensitized with docetaxel-BSA as described in Examples 12 and 13. The antibody screening assay was performed by diluting the antisera containing docetaxel antibodies to 1:100, 1:1,000, 1:10, 000 and 1:100,000 in phosphate buffered saline containing 0.1% BSA and 0.01% thimerosal. To each well of docetaxel-BSA sensitized wells (prepared in Examples 12 and 13) 100 µL of diluted antibody was added and incubated for 10 minutes at room temperature with shaking. During this incubation antibody binds to the docetaxel-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of docetaxel antibody bound to the docetaxel-BSA conjugate in the wells, 100 µL of a goat anti-mouse antibody—HRP enzyme conjugate (Jackson Immunoresearch) diluted to a predetermined specific activity (approximately 1/2400) in PBS with 0.1% BSA, 0.01% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to docetaxel antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm with a 96-well plate reader. The amount of antibody in a well was proportional to the absorbance measured and was expressed as the dilution (titer) resulting in an absorbance of 1.5. Titers were determined by graphing log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in Examples 15 and 16.

Example 14b

Antibody Screening Procedure—Monoclonal Screening

Antibodies were screened by Enzyme-Linked Immunosorbent Assay (ELISA) method. This method for screening docetaxel monoclonal antibodies (produced in Example 11) was performed with the microtiter plates that were sensitized with docetaxel C7 substituted-BSA (Example 8) as described in Example 13. To each well of docetaxel C7 substituted-BSA sensitized wells (prepared in Example 13) 50 μL phosphate buffered saline containing 0.1% BSA and 0.01% thimerosal and then 50 μL of monoclonal culture supernatant were added and incubated for 10 minutes at room temperature with shaking. During this incubation antibody binds to the docetaxel C7 substituted-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of docetaxel antibody bound to the docetaxel C7 substituted-BSA conjugate in the wells, 100 μL of a goat anti-mouse antibody—HRP enzyme conjugate (Jackson Immunoresearch) diluted to a predetermined specific activity (approximately 1/2400) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to doxorubicin antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate), a substrate for HRP, to develop color during a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm on a 96-well plate reader. The amount of antibody in a well was proportional to the absorbance measured. Samples with an absorbance of three times background or greater were designated as positive.

Example 15

Indirect Competitive Microtiter Plate Immunoassay Procedure Determining $IC_{50}$ and Cross-Reactivity for Antibodies to C7, C10 Docetaxel Di-acid Derivative Conjugate Docetaxel concentrations were measured by an indirect competitive Enzyme-Linked Immunosorbent Assay (ELISA) method. This method for measuring docetaxel concentrations was performed with the microtiter plates that were sensitized with docetaxel-BSA described in Example 13. Docetaxel, paclitaxel, and 10-O-deactylbaccatin III were diluted 10 fold in PBS with 0.1% BSA and 0.01% Thimerosal over a concentration range of 0.01 to 10,000 ng/mL. The assay was performed by incubating 50 μL of the analytes to be measured with 50 μL of antibody (produced in Example 10 with immunogen of Example 5) diluted to a titer determined in Example 14a. During the 10 minute incubation (R.T., with shaking) there is a competition of antibody binding for the docetaxel conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of docetaxel antibody bound to the docetaxel-BSA conjugate in the wells, 100 μL of a goat anti-mouse antibody—HRP enzyme conjugate (Jackson Immunoresearch) diluted to a predetermined specific activity (approximately 1/2400) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to docetaxel antibodies in the wells, the plates were again washed three times to remove unbound secondary conjugate. To develop a measurable color in the wells washing was followed by the addition of 100 μL of TMB (TMB Liquid Substrate) a substrate for HRP, to develop color in a 10 minute incubation with shaking at room temperature. Following the incubation for color development, 50 μL of stop solution (1.5% sodium fluoride in di $H_2O$) was added to each well to stop the color development and after 10 seconds of shaking the absorbance was determined at 650 nm with a 96-well plate reader. The amount of antibody in a well was proportional to the absorbance measured and inversely proportional to the amount of docetaxel in the sample. The absorbance of the color in the wells containing analyte was compared to that with no analyte and a standard curve was generated. The $IC_{50}$ value for a given analyte was defined as the concentration of analyte that is required to inhibit 50% of the absorbance from the wells containing no analyte. The cross-reactivity of a given analyte was calculated as the ratio of the $IC_{50}$ for docetaxel to the $IC_{50}$ for Paclitaxel and 10-O-Deactylbaccatin III expressed as a percent. When measured with an antibody as produced in Example 10 with immunogen of Example 4 and 5 the antibodies with percent cross-reactivates relative to docetaxel for Paclitaxel and 10-O-Deactylbaccatin III</=6% were obtained.

Example 16

Indirect Competitive Microtiter Plate Immunoassay Procedure Determining IC$_{50}$ and Cross-Reactivity for Antibodies to C7 Substituted Docetaxel Acid Derivative Conjugate Docetaxel concentrations were measured by an indirect competitive Enzyme-Linked Immunosorbent Assay (ELISA) method. This method for measuring docetaxel concentrations was performed with the microtiter plates that were sensitized with docetaxel-BSA described in Example 13 for monoclonal antibodies and in Examples 12 and 13 for polyclonal antibodies. Docetaxel, paclitaxel, and 10-O-deactylbaccatin III were diluted 10 fold in PBS with 0.1% BSA and 0.01% Thimerosal over a concentration range of 0.01 to 10,000 ng/mL. The assay was performed by incubating 50 µL of the analytes to be measured with 50 µL of antibody (produced in Example 11) diluted to a titer determined in Example 14a. During the 10 minute incubation (R.T., with shaking) there is a competition of antibody binding for the docetaxel conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of docetaxel antibody bound to the docetaxel-BSA conjugate in the wells, 100 µL of a goat anti-mouse antibody—HRP enzyme conjugate (Jackson Immunoresearch) diluted to a predetermined specific activity (approximately 1/2400) in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to docetaxel antibodies in the wells, the plates were again washed three times to remove unbound secondary conjugate. To develop a measurable color in the wells washing was followed by the addition of 100 µL of TMB (TMB Liquid Substrate), a substrate for HRP, to develop color in a 10 minute incubation with shaking at room temperature. Following the incubation for color development, 50 µL of stop solution (1.5% sodium fluoride in di H$_2$O) was added to each well to stop the color development and after 10 seconds of shaking the absorbance was determined at 650 nm on a 96 well plate reader. The amount of antibody in a well was proportional to the absorbance measured and inversely proportional to the amount of docetaxel in the sample. The absorbance of the color in the wells containing analyte was compared to that with no analyte and a standard curve was generated. The IC$_{50}$ value for a given analyte was defined as the concentration of analyte that is required to inhibit 50% of the absorbance for the wells containing no analyte. The cross-reactivity of a given analyte was calculated as the ratio of the IC$_{50}$ for docetaxel to the IC$_{50}$ for Paclitaxel, and 10-O-Deactylbaccatin III expressed as a percent. When measured with an antibody as produced in Example 11 with immunogen of Example 9a, on a microtiter plate prepared as in Example 12 the percent cross-reactivates relative to docetaxel for Paclitaxel was less than 2%, and for 10-O-Deactylbaccatin III less than 0.02%. When measured with an antibody as produced in Example 11 with immunogen of Example 9a, on a microtiter plate prepared as in Example 13 the percent cross-reactivates relative to docetaxel for Paclitaxel was less than 1%, and for 10-O-Deacytlbaccatin III less than 0.01% were obtained. When measured with a monoclonal antibody as produced in Example 11 with immunogen of Examples 9a & 9b, on a microtiter plate prepared as in Example 13 the percent cross-reactivates relative to docetaxel for paclitaxel was less than 12%, and for 10-O-Deacytlbaccatin III less than 1.0%.

What is claimed:

1. An immunoassay process for detecting docetaxel in a sample comprising providing a mixture containing a sample, an antibody reactive with docetaxel and not substantially reactive with paclitaxel and 10-O-deacetylbaccatin III, and a compound conjugated with a carrier wherein the compound is selected from those represented by the formula:

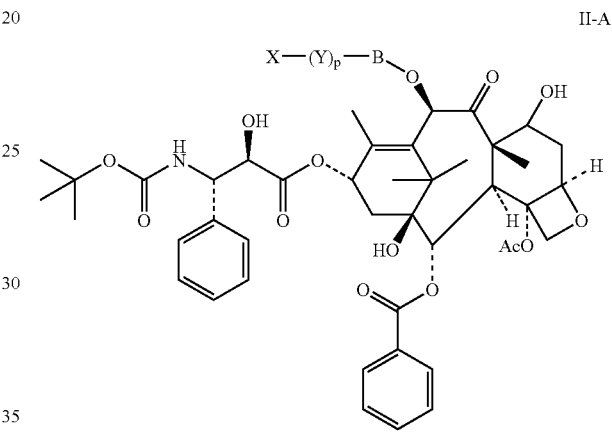

II-A wherein B is

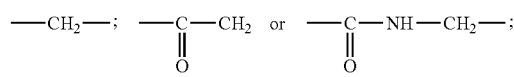

Y is an organic spacing group;
X is a functional group capable of linking to a carrier; and
p is an integer from 0 to 1;
a compound of the formula:

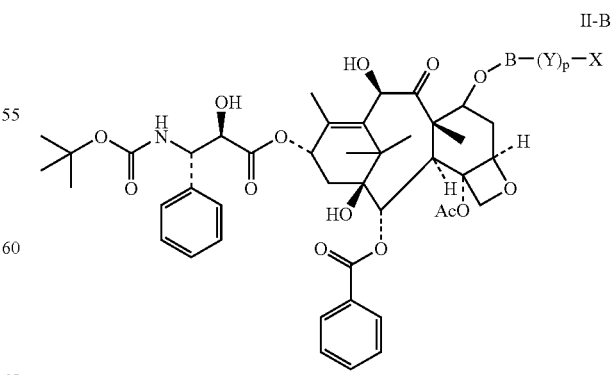

II-B wherein B, X, Y and p are as above;

a compound of the formula

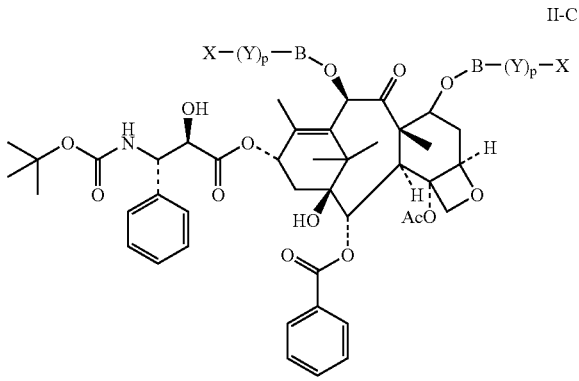

II-C wherein B, X, Y and p are as above,
and mixtures thereof,
causing the docetaxel in the sample and said conjugate to bind with said antibody and thereafter measuring the amount of said conjugate in said mixture which is bound or unbound to said antibody whereby the presence of docetaxel in the sample can be determined.

2. The immunoassay process of claim 1, wherein the sample is a human sample.

3. The immunoassay process of claim 2, wherein said antibody is generated from an immunogen comprising an immunogenic carrier linked to a ligand selected from the group consisting of a compound of the formula:

II-A

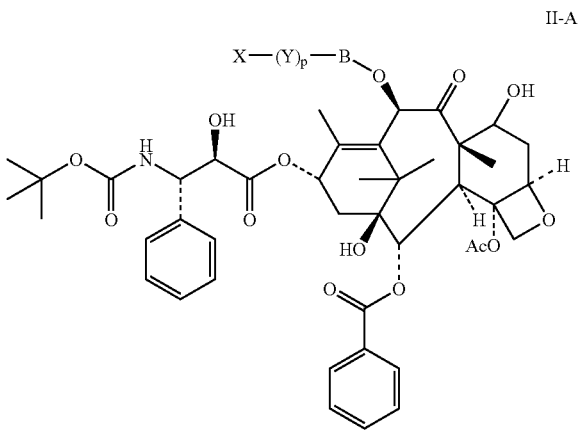

wherein p, Y and B are as defined in claim 1, and
X is a functional group capable of linking to a carrier;
a compound of the formula:

II-B

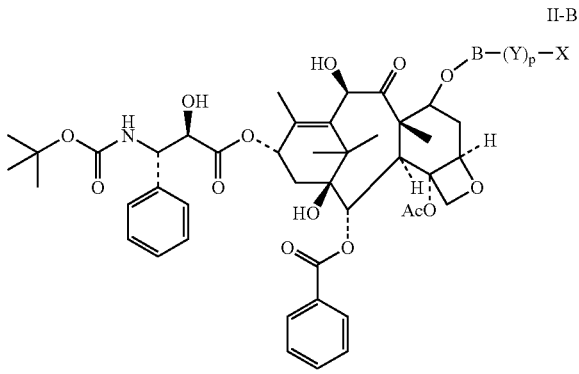

wherein B, X, Y and p are as above;

a compound of the formula

II-C

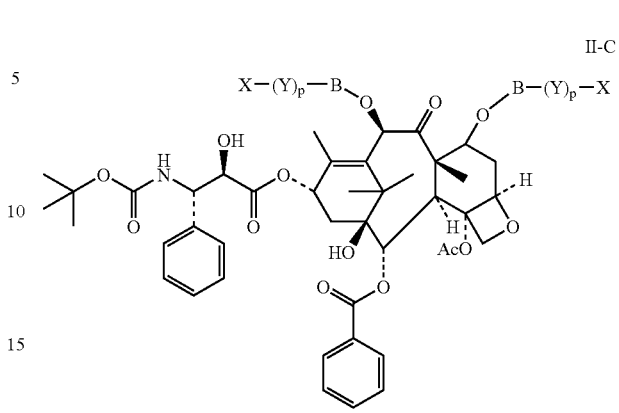

wherein B, X, Y and p are as above,
and mixtures thereof.

4. The immunoassay process of claim 2, wherein the antibody is attached to a solid support.

5. The immunoassay process of claim 4, wherein the solid support is microtitor plates.

6. The immunoassay process claim 4, wherein the solid support is nanoparticles.

7. The immunoassay process of claim 6, wherein said antibody is derived from mice, rabbits or rats.

8. The immunoassay process of claim 7, wherein said antibody is a monoclonal antibody.

9. The immunoassay process of claim 3, wherein said antibody is derived from an immunogen of an immunogenic carrier with a ligand of the formula:

II-A

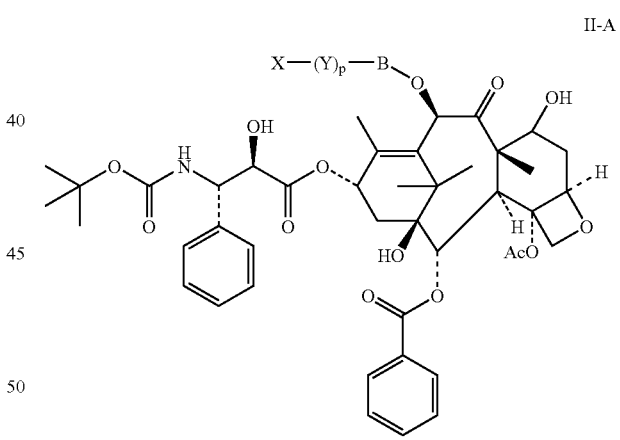

wherein B is $$-CH_2-; \quad -\underset{\underset{O}{\|}}{C}-CH_2-; \quad \text{or} \quad -\underset{\underset{O}{\|}}{C}-NH-CH_2-;$$

Y is an organic spacing group;
X is a functional group capable of linking to a carrier; and
p is an integer from 0 to 1.

10. The immunoassay process of claim 9, wherein said antibody is derived from mice, rabbits or rats.

11. The immunoassay process of claim 9, wherein said antibody is a monoclonal antibody.

12. The immunoassay process of claim 3, wherein said antibody is derived from an immunogen of an immunogenic carrier with a ligand of the formula:

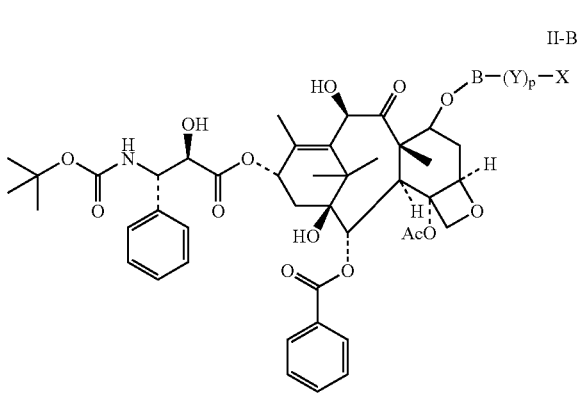

II-B wherein B, X, Y and p are as defined in claim 1.

13. The immunoassay process of claim 12, wherein said antibody is derived from mice, rabbits or rats.

14. The immunoassay process of claim 13, wherein said antibody is a monoclonal antibody.

15. The immunoassay process of claim 3, wherein said antibody is derived from an immunogen of an immunogenic polyamine polymer and a ligand of the formula:

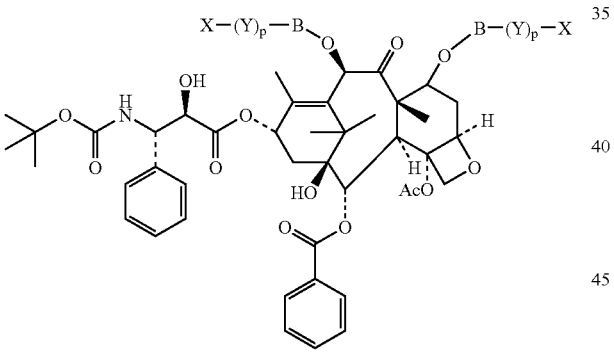

II-C wherein B, X, Y and p are as defined in claim 1.

16. The immunoassay process of claim 15, wherein said antibody is derived from mice, rabbits or rats.

17. The immunoassay process of claim 15, wherein said antibody is a monoclonal antibody.

18. A kit for determining the presence of docetaxel in a patient sample comprising reagents packed in separate containers, one of the reagents being an antibody reactive with docetaxel and not substantially reactive with paclitaxel and 10-O-deacetylbaccatin III, and the other reagent being a compound conjugated with a carrier wherein the compound is selected from those represented by the formula:

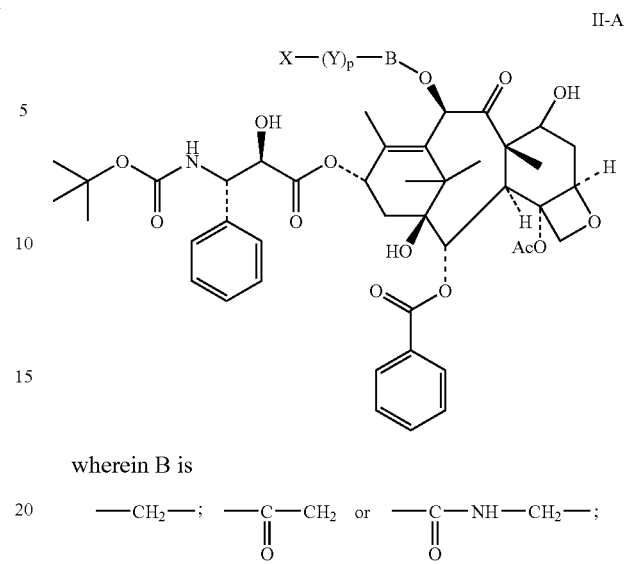

II-A wherein B is $-CH_2-$;  $-\underset{\underset{O}{\|}}{C}-CH_2-$ or $-\underset{\underset{O}{\|}}{C}-NH-CH_2-$;

Y is an organic spacing group;
X is a functional group capable of linking to a carrier; and
p is an integer from 0 to 1;
a compound of the formula:

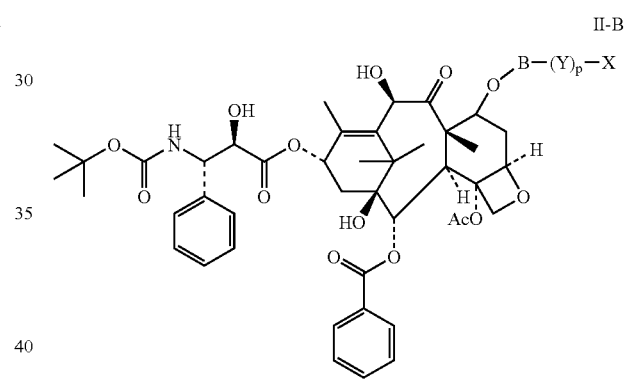

II-B wherein B, X, Y and p are as above;
a compound of the formula

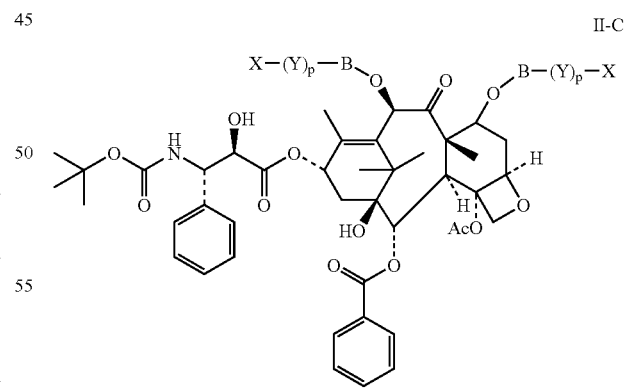

II-C wherein B, X, Y and p are as above;
and mixtures thereof.

* * * * *